(12) United States Patent
Vandesteeg et al.

(10) Patent No.: US 8,178,120 B2
(45) Date of Patent: *May 15, 2012

(54) METHODS FOR PROCESSING SUBSTRATES HAVING AN ANTIMICROBIAL COATING

(75) Inventors: Nathan A. Vandesteeg, Deerfield, IL (US); John-Bruce D. Green, Buffalo Grove, IL (US); Vadim V. Krongauz, Bartlett, IL (US); Phillip W. Carter, Round Lake, IL (US); Dustin C. Cawthon, Crystal Lake, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 151 days.

This patent is subject to a terminal disclaimer.

(21) Appl. No.: 12/143,304

(22) Filed: Jun. 20, 2008

(65) Prior Publication Data

US 2009/0317435 A1  Dec. 24, 2009

(51) Int. Cl.
*A01N 25/34* (2006.01)
*A61K 33/24* (2006.01)
*A61K 33/38* (2006.01)
*A61K 33/14* (2006.01)
*A01N 59/16* (2006.01)
*A01N 59/12* (2006.01)

(52) U.S. Cl. ........ 424/411; 424/617; 424/618; 424/663; 424/669

(58) Field of Classification Search .......................... None
See application file for complete search history.

(56) References Cited

U.S. PATENT DOCUMENTS

| | | | |
|---|---|---|---|
| 1,610,391 A | 12/1926 | Smith | |
| 1,783,334 A | 12/1930 | Keelan | |
| 3,856,805 A | 12/1974 | Margraf | |
| 3,932,627 A | 1/1976 | Margraf | |
| 4,045,400 A | 8/1977 | Korshak et al. | |
| 4,412,834 A | 11/1983 | Kulin et al. | |
| 4,417,890 A | 11/1983 | Dennehey et al. | |
| 4,440,207 A | 4/1984 | Genatempo et al. | |
| 4,457,749 A | 7/1984 | Bellotti et al. | |
| 4,485,064 A | 11/1984 | Laurin | |
| 4,581,028 A | 4/1986 | Fox, Jr. et al. | |
| 4,592,920 A | 6/1986 | Murtfeldt | |
| 4,603,152 A | 7/1986 | Laurin et al. | |
| 4,632,844 A | 12/1986 | Yanagihara et al. | |
| 4,738,668 A | 4/1988 | Bellotti et al. | |
| 4,990,363 A | 2/1991 | Suhr et al. | |
| 5,019,096 A | 5/1991 | Fox, Jr. et al. | |
| 5,236,703 A * | 8/1993 | Usala ......................... | 424/78.36 |
| 5,242,532 A | 9/1993 | Cain | |
| 5,360,413 A | 11/1994 | Leason et al. | |
| 5,614,568 A | 3/1997 | Mawatari et al. | |
| 5,616,338 A | 4/1997 | Fox, Jr. et al. | |
| 5,630,804 A | 5/1997 | Imada et al. | |
| 5,643,190 A | 7/1997 | Utterberg | |
| 5,718,694 A | 2/1998 | Rupp | |
| 5,730,418 A | 3/1998 | Feith et al. | |
| 5,744,151 A | 4/1998 | Capelli | |
| 5,782,816 A | 7/1998 | Werschmidt et al. | |
| 5,863,548 A | 1/1999 | Elder | |
| 5,928,174 A | 7/1999 | Gibbins | |
| 5,948,385 A | 9/1999 | Chapman et al. | |
| 6,030,632 A | 2/2000 | Sawan et al. | |
| 6,039,302 A | 3/2000 | Cote, Sr. et al. | |
| 6,103,868 A | 8/2000 | Heath et al. | |
| 6,106,505 A | 8/2000 | Modak et al. | |
| 6,113,636 A | 9/2000 | Ogle | |
| 6,126,931 A | 10/2000 | Sawan et al. | |
| 6,150,430 A | 11/2000 | Walters et al. | |
| 6,180,584 B1 | 1/2001 | Sawan et al. | |
| 6,246,824 B1 | 6/2001 | Vandeberg et al. | |
| 6,264,936 B1 | 7/2001 | Sawan et al. | |
| 6,265,476 B1 | 7/2001 | Krongauz et al. | |
| 6,267,782 B1 | 7/2001 | Ogle et al. | |
| 6,323,256 B1 | 11/2001 | DelMain | |
| 6,329,488 B1 | 12/2001 | Terry et al. | |
| 6,355,858 B1 | 3/2002 | Gibbins | |
| 6,443,980 B1 | 9/2002 | Wang et al. | |
| 6,465,167 B2 | 10/2002 | Whitcomb et al. | |
| 6,472,451 B2 | 10/2002 | Ha et al. | |
| 6,480,250 B1 | 11/2002 | Matsufuji et al. | |
| 6,497,901 B1 | 12/2002 | Royer | |
| 6,506,293 B1 | 1/2003 | Rumpf | |
| 6,506,814 B2 | 1/2003 | Krongauz et al. | |
| 6,530,951 B1 | 3/2003 | Bates et al. | |
| 6,548,121 B1 | 4/2003 | Bauer et al. | |
| 6,565,913 B2 | 5/2003 | Arps et al. | |
| 6,579,539 B2 | 6/2003 | Lawson et al. | |
| 6,592,814 B2 | 7/2003 | Wilcox et al. | |
| 6,596,401 B1 | 7/2003 | Terry et al. | |
| 6,605,751 B1 | 8/2003 | Gibbins et al. | |
| 6,645,444 B2 | 11/2003 | Goldstein | |
| 6,669,681 B2 | 12/2003 | Jepson et al. | |
| 6,682,509 B2 | 1/2004 | Lopez | |
| 6,706,201 B1 | 3/2004 | Meyer et al. | |
| 6,716,891 B1 | 4/2004 | Meisenburg et al. | |
| 6,716,895 B1 | 4/2004 | Terry | |
| 6,780,332 B2 | 8/2004 | Shiau et al. | |
| 6,783,690 B2 | 8/2004 | Kologe et al. | |

(Continued)

FOREIGN PATENT DOCUMENTS

CN  1873048  * 12/2006

(Continued)

OTHER PUBLICATIONS

Elliott (Intensive Care Med 2000, 26, S45-S50).*

(Continued)

*Primary Examiner* — Mina Haghighatian
*Assistant Examiner* — Jessica Kassa
(74) *Attorney, Agent, or Firm* — Marshall, Gerstein & Borun LLP

(57) ABSTRACT

Methods for processing substrate surfaces carrying coatings comprising a metal are disclosed. The methods involve providing a substrate surface having a coating comprising a metal, and exposing the substrate surface to a mixture including an oxidizing agent and an anion.

27 Claims, No Drawings

U.S. PATENT DOCUMENTS

| | | | |
|---|---|---|---|
| 6,800,278 B1 | 10/2004 | Perrault et al. |
| 6,849,214 B2 | 2/2005 | Patil |
| 6,852,771 B2 | 2/2005 | Balch et al. |
| 6,878,757 B2 | 4/2005 | Roby |
| 6,897,349 B2 | 5/2005 | Gibbins et al. |
| 6,908,681 B2 | 6/2005 | Terry et al. |
| 6,921,390 B2 | 7/2005 | Bucay-Couto et al. |
| 6,949,598 B2 | 9/2005 | Terry |
| 6,984,392 B2 | 1/2006 | Bechert et al. |
| 7,179,849 B2 | 2/2007 | Terry |
| 7,232,777 B1 | 6/2007 | Van Hyning |
| 7,288,264 B1 | 10/2007 | Sawan et al. |
| 7,345,980 B2 | 3/2008 | Richard |
| 7,378,156 B2 | 5/2008 | Terry |
| 2001/0023250 A1 | 9/2001 | Spada et al. |
| 2003/0031872 A1 | 2/2003 | Arps et al. |
| 2003/0129322 A1 | 7/2003 | Kunz et al. |
| 2003/0141477 A1 | 7/2003 | Miller |
| 2003/0157147 A1* | 8/2003 | Hoge et al. | 424/443 |
| 2003/0157176 A1 | 8/2003 | Nakamura et al. |
| 2003/0165633 A1 | 9/2003 | Ryu et al. |
| 2003/0198821 A1 | 10/2003 | Terry et al. |
| 2003/0208165 A1 | 11/2003 | Christensen et al. |
| 2004/0052831 A1 | 3/2004 | Modak et al. |
| 2004/0106341 A1 | 6/2004 | Vogt et al. |
| 2004/0229034 A1* | 11/2004 | Djokic | 428/328 |
| 2005/0003019 A1 | 1/2005 | Petersen |
| 2005/0008676 A1 | 1/2005 | Qiu et al. |
| 2005/0013842 A1 | 1/2005 | Qiu et al. |
| 2005/0019533 A1 | 1/2005 | Mossbrook et al. |
| 2005/0064176 A1 | 3/2005 | Terry |
| 2005/0147919 A1 | 7/2005 | Kunz et al. |
| 2005/0147979 A1 | 7/2005 | Koo et al. |
| 2005/0226931 A1 | 10/2005 | Gibbins et al. |
| 2006/0068024 A1 | 3/2006 | Schroeder et al. |
| 2006/0085036 A1 | 4/2006 | Viola |
| 2006/0090596 A1* | 5/2006 | Goia et al. | 75/371 |
| 2006/0140994 A1 | 6/2006 | Bagwell et al. |
| 2006/0141015 A1 | 6/2006 | Tessier et al. |
| 2006/0167180 A1 | 7/2006 | Plaut et al. |
| 2006/0216327 A1 | 9/2006 | Madsen et al. |
| 2006/0222971 A1 | 10/2006 | Seo et al. |
| 2006/0257681 A1 | 11/2006 | Wolf et al. |
| 2006/0269485 A1 | 11/2006 | Friedman et al. |
| 2007/0003603 A1 | 1/2007 | Karandikar et al. |
| 2007/0048356 A1 | 3/2007 | Schorr et al. |
| 2007/0050007 A1 | 3/2007 | Kondyurin et al. |
| 2007/0085036 A1 | 4/2007 | Santhouse |
| 2007/0098806 A1 | 5/2007 | Ismail et al. |
| 2007/0154506 A1 | 7/2007 | Patton et al. |
| 2007/0207335 A1 | 9/2007 | Karandikar et al. |
| 2007/0212381 A1 | 9/2007 | DiFiore et al. |
| 2007/0254044 A1 | 11/2007 | Karandikar et al. |
| 2008/0021381 A1 | 1/2008 | Lurvey et al. |
| 2008/0021392 A1 | 1/2008 | Lurvey et al. |
| 2008/0027410 A1 | 1/2008 | Harding et al. |
| 2008/0063693 A1 | 3/2008 | Cook et al. |
| 2008/0181931 A1 | 7/2008 | Qiu et al. |
| 2009/0314628 A1 | 12/2009 | Lee et al. |
| 2009/0324666 A1 | 12/2009 | Krongauz et al. |
| 2009/0324738 A1 | 12/2009 | Krongauz |

FOREIGN PATENT DOCUMENTS

| | | |
|---|---|---|
| CN | 18734048 | 12/2006 |
| EP | 0190504 | 8/1986 |
| EP | 0328421 | 8/1989 |
| GB | 2000788 | 1/1979 |
| JP | 2007182605 | 7/2007 |
| WO | WO-94/22522 | 10/1994 |
| WO | WO-01/43788 | 6/2001 |
| WO | WO-02/083156 | 10/2002 |
| WO | WO-2006/026026 | 3/2006 |
| WO | WO 2006/026026 * | 3/2006 |
| WO | WO-2006/056482 A1 | 6/2006 |
| WO | WO-2006/067061 | 6/2006 |
| WO | WO-2006/074117 A2 | 7/2006 |
| WO | WO-2006074117 * | 7/2006 |
| WO | WO-2006/099906 | 9/2006 |
| WO | WO-2007/000590 | 1/2007 |
| WO | WO-2007/028607 | 3/2007 |
| WO | WO-2007/070649 | 6/2007 |
| WO | WO-2007095058 A2 | 8/2007 |
| WO | WO-2007/104107 | 9/2007 |
| WO | WO-2008/031601 | 3/2008 |
| WO | WO-2008/036377 | 3/2008 |
| WO | WO-2008/068154 | 6/2008 |
| WO | WO-2008/145750 | 12/2008 |
| WO | WO-2009154905 A1 | 12/2009 |

OTHER PUBLICATIONS

Lok et al. (J. Biol. Inorg. Chem. 2007 12, 527-534).*
Schwartz (Encyclopedia of Materials, Parts and Finishes Second Edition CRC Press: Boca Raton, FL 2002, p. 857).*
Okamoto et al. (Optics Letters 2000, 25, 372-374).*
Tang et al. (Smart Structures and Materials 2006: Sensors and Smart Structures Technologies for Civil Mechanical and Aerospace Systems 2006, Proc. of SPIE 6174 61743R).*
Kim et al., Antimicrobial effects of silver nenoparticles, *Nanomed.:. Nanotechnol. Biol. Med.*, 3:95-101 (2007).
Belfield et al., *Photoinitiated Polymerization*, ACS Symposium Series 847, American Cancery Society, Washington DC (2003).
Brown (ed.), *Chemistry: The Central Science*, 6th edition, Prentice Hall (2002).
Dean, Table 8.6, IN: *Lange's Handbook of Chemistry*, 15th ed., McGraw Hill (1998).
Fan et al., "Chemical, electrochemical, gravimetric, and microscopic studies on antimicrobial silver films", *J. Phys. Chem. B*, 106:279-87 (2002).
Jacobs et al., "Thermodynamics of complex formation reactions in non-aqueous solvents : Part 2. Reaction of silver(I) with $N,N,N',N'$-tetramethylene diamine in acetone, methanol and ethanol", *Thermochimica Acta*, 127:399-402 (1988).
Kampf et al., "Microbicidal activity of a new silver-containing polymer, SPI-ARGENT II", *Antimicrob Agents Chemother.*, 42:2440-2 (1998).
Kapoor, "Preparation, characterization, and surface modification of silver particles," *Langmuir*, 14:1021-5 (1998).
Kashiwagi et al., "Facile size-regulated synthesis of silver nanoparticles by controlled thermolysis of silver alkylcarboxylates in the presence of alkylamines with different chain lengths", *J. Colloid Interface Sci.*, 300:169-75 (2006).
Klang, *Radiation Curable Hyperbranched Polyester Acrylates*, Sartomer Company, Exton, Pennsylvania (Mar. 2008) (6 pp.).
Klasen, "A historical review of the use of silver in the treatment of burns. II. Renewed interest for silver", *Burns*, 26:131-8 (2000).
Krongauz et al., *Processes in Photoreactive Polymers*, New York, NY: Chappman & Hall (1995).
Russell et al., "Antimicrobial activity and action of silver", *Prog. Med. Chem.*, 31:351-70 (1994).
Sartomer Co. Product Bulletin, *Hydrophilic vs. Hydrophobic Monomers* (Exton, Penn.) Dec. 2004 (8 pp.).
*Solubility Product Constants*, from University of Split Faculty of Chemistry and Technology website <URL:http://www.ktf-split.hr> downloaded Jun. 16, 2008 (6 pp.).
Van Poucke, "The thermodynamics of ethylene-diaminc complexes of silver," *Talanta*, 23:161-2 (1976).
Yamamoto et al., "Size-controlled synthesis of monodispersed silver nanoparticles capped by long-chain alkyl carboxylates from silver carboxylate and tertiary amine," *Langmuir*, 22:8581-6 (2006).
Zwanenburg, *How to Formulate UV-Curing Coatings*, (Verneuil en Hallatte, France (2008) (20 pp).
Bacterin International Inc., *Bacterin: The Smart Coating*, Slide Presentation (8 pages).
Bailey et al., "The electrochemistry and kinetics of the silver-triiodide reaction," *Electrochimica Acta*, 22:35-40 (1977).
Broome et al. "Complex formation with high molecular weight amines. I." *J. Am. Chem. Soc.*, 68:67-69 (1946).
Campbell et al., "The chemical iodination of silver," *Australian J. Chem.*, 39:827-837 (1986).

Clement et al., "Antibacterial silver," *Metal Based Drugs*, 1:467-482 (1994).

Dai et al., "2D and 3D silver(I) ethylenediamine coordination polymers with Ag-Ag argentophilic interaction," *Z. Naturforsch*, 62b: 1112-1116 (2007).

Dong et al., Silver carboxylate nanostructure nucleation and growth on AgBr crystals, *Nanotechnology*, 16:S592-S600 (2005).

Duff et al., "The microstructure of colloidal silver: evidence for a polytetrahedral growth sequence," *J. Chem. Soc., Chem. Comm.*, 16:1264-1266 (1987).

Hozumi et al., "Spatially defined silver mirror reaction on micropatterned aldehyde-terminated self-assembled monolayer," *Appl. Surface Science*, 252:6111-6114 (2006).

Kang et al., Surface chemistry of ethylenediamine ($NH_2$-$CH_2CH_2NH_2$) on Pt(111), *Surface Science*, 470: L13-L19 (2000).

Lansdown, "Silver in health care: antimicrobial effects and safety in use," in: Hipler et al. (eds.), Biofunctional Textiles and the Skin. *Curr. Probl. Dermatol.* Basel: Karger, 33:17-34 (2006).

Magyar et al., "The silver(I) complexes of ethylenediamine in solution," *Acta Chem. Scand. A*, 32:943-955 (1978).

Mills et al., "Formation of $\mu_2,\eta^2$-Diaminoethylene ($H_2NCCNH_2$) from Cyanogen ($C_2N_2$) and Hydrogen on Pt(111): Characterization of a Diiminium Surface Species," *J. Am. Chem. Soc.*, 118:6524-6525 (1996).

Newman et al., "The infrared spectra and structures of some silver-ethylenediamine complexes," *J. Chem. Soc.*, 3447-3450 (1962).

Nielsen et al., "The basis for colored silver-protein complex formation in stained polyacrylamide gels," *Anal. Biochem.*, 141:311-315 (1984).

Olson et al., "The simple yet elusive crystal structure of silver acetate and the role of the Ag-Ag bond in the formation of silver nanoparticles during the thermally induced reduction of silver carboxylates" *Chem. Mater.*, 18:1667-1674 (2006).

Patra et al., "The synthesis and characterization of a series of bis-bidentate Schiff base ligands and their coordination complexes with silver(I), copper(I) and zinc(II) d10 metal ions," *New J. Chem.*, 27:1124-1131 (2003).

Qu et al., "Novel silver nanostructures from silver mirror reaction on reactive substrates," *J. Phys. Chem. B*, 109:13985-13990 (2005).

Qu et al., "Synthesis and crystal structure of copper II and silver I complex with 1,4-diazabicyclo[2.2.2]octane[Cu(CBC)$_2$(Dabco)($H_2O$)] $n$ (1) and [Ag$_2$(HBC)$_2$(Dabco)] n (2)," *J. Chem. Crystallogr.* 37: 579-582 (2007).

Rabii et al., "Measurement and control of thin film uniformity in hollow glass waveguides," *Opt. Eng.*, 38:2009-2015 (1999).

Richards et al., Chapter I: Synthetic approaches to metallic nanomaterials, in: Kumar et al. (eds.), *Nanofabrication Towards Biomedical Applications: Techniques, Tools, Applications, and Impact*, 1st edition, Wiley-VCH, pp. 3-32 (2005).

Ross et al., *Colloidal Systems and Interfaces*, J. Wiley & Sons (1988).

Satoshi et al., "Bleach-fixer using a new biodegradable chelating agent," *Konika Technical Report*, 16:13-18 (2003).

Southeast Missouri State University, *CH186 Lecture Presentation: Transition Metal/Coordination Chemistry*. Retrieved from the Internet, Nov. 3, 2008: <URL: http://chemistry.semo.edu/crawford/ch186/lectures/ch20/>.

Starovoytov et al., "Dissolution behavior of silver in ammoniacal solutions using bromine, iodine and hydrogen-peroxide as oxidants," *Hydrometallurgy*, 86:114-119 (2007).

Tammann et al., "Uber anlauffarben von metallen," *Allg. Chem.*, 111:78-89 (1920). [German Only].

University of Waterloo, *Coordination Chemistry (CaCt)*. Retrieved from the Internet, Nov. 10, 2008: <URL: http://www.science.uwaterloo.ca/~cchieh/cact/cact.html>.

University of Waterloo, *Cyberspace Chemistry (CaCt)*. Retrieved from the Internet, Nov. 3, 2008: <URL: http://www.science.uwaterloo.ca/~cchieh/cact/cact.html>.

Yilmaz et al., "Silver(I) saccharinato complexes with ethylenediamine and *N,N*-Dimethylethylenediamine—[Ag$_2$(sac)$_2$(en)($H_2O$]$_n$ and [Ag$_2$ (sac) $_2$ (dmen) $_2$]," *Z. Anorg. Allg. Chem.*, 631:1961-1965 (2005).

Zhai et al., "Silver colloids and interfacial colloids-adsorption of alizarin yellow 2G and its effect on colloidal nulcleation," *Langmuir*, 13:420-425 (1997).

Final office action, U.S. Appl. No. 12/143,319, dated Feb. 17, 2012.

Nonfinal office action, U.S. Appl. No. 12/400,439, dated Dec. 23, 2011.

Nonfinal office action, U.S. Appl. No. 12/145,548, dated Dec. 5, 2011.

Lok et al., Silver nanoparticles: partial oxidation and antibacterial activities, J. Biol. Inorg. Chem., 12:527-34 (2007).

Final office action from U.S. Appl. No. 12/164,414, dated Feb. 25, 2011.

Partial English Translation of Japanese Patent No. JP8133919A (6 pages).

Partial English Translation of Japanese Patent No. JP56-82504A (2 pages).

International Search Report and Written Opinion for corresponding International Application No. PCT/US2009/043947, dated Jul. 26, 2010 (10 pp.).

Copending U.S. Appl. No. 12/400,439 (Carter et al.), filed Mar. 9, 2009.

Humar et al., Prospective randomized trial of 10% povidone-iodine versus 0.5% tincture of chlorhexidine as cutaneous antisepsis for prevention of central venous catheter infection, *Clinical Infectious Diseases*, 31:1001-7 (2000).

Office action (nonfinal) from U.S. Appl. No. 12/164,414, dated Apr. 30, 2010.

O'Grady et al., *Guidelines for the Prevention of Intravascular Catheter-Related Infections*, MMWR Recommendations and Reports, 51(RR10):1-26 (Aug. 9, 2002).

Nonfinal office action from U.S. Appl. No. 12/145,548, dated May 13, 2011.

Nonfinal office action from U.S. Appl. No. 12/143,319, dated Oct. 15, 2010.

International Search Report and Written Opinion for corresponding International Application No. PCT/US2009/043947, dated Jul. 26, 2010 (10 pages).

\* cited by examiner

METHODS FOR PROCESSING SUBSTRATES HAVING AN ANTIMICROBIAL COATING

BACKGROUND

1. Field of the Disclosure

The disclosure relates generally to methods for processing substrates carrying coatings comprising a metal. More particularly, the disclosure is directed to methods of processing substrates, such as medical devices, carrying coatings comprising a metal and having antimicrobial activity.

2. Brief Description of Related Technology

Even brief exposure to surfaces contaminated with microbes can introduce bacterial, viral, fungal, or other undesirable infections to humans and other animals. Of particular concern is preventing or reducing microbial infection associated with the use of invasive medical devices such as catheters, intravenous fluid administration systems, and other medical devices which require prolonged patient contact and thus present significant infection risks. Contamination may result from the patients' own flora or from one or more healthcare workers' hands during insertion and/or manipulation of the device, or from both the patient and the healthcare worker. Medical devices coated with antimicrobial materials can reduce the transfer of such microbes to patients, thereby improving the safety and efficacy of these devices. Such antimicrobial coatings often include silver metal or silver salts, or other metals with demonstrable antimicrobial activity such as copper, gold, zinc, cerium, platinum, palladium, or tin.

Silver and salts thereof are commonly used in antimicrobial coatings because of their demonstrated broad spectrum antimicrobial activity against various bacteria, viruses, yeast, fungi, and protozoa. It is theorized that the observed antimicrobial activity is primarily due to the ability of silver ions to tightly bind nucleophilic functional groups containing sulfur, oxygen or nitrogen. Many nucleophilic functional groups such as thiols, carboxylates, phosphates, alcohols, amines, imidazoles, and indoles are prevalent in biomolecules. Upon binding of ionized silver to these various nucleophilic functional groups, it is believed that widespread disruption and inactivation of microbial biomolecules (and thus antimicrobial activity) occurs.

Silver and salts thereof have therefore been used as antimicrobial agents in a wide variety of applications; for example, they have been incorporated in the absorbent materials of wound care products such as dressings, gels, and bandages, and also in compositions for providing antimicrobial coatings on medical devices. One disadvantage of some metallic silver-containing antimicrobial coatings, however, is their color/opaqueness, which prevents a healthcare provider from being able to see through the medical device substrate. Coatings comprising metallic silver, for example, can be brown in color. Thus, when such colored coatings are applied to transparent surfaces, the coated surfaces typically have a brown color and significantly diminished transparency.

In contrast to coatings comprising metallic silver, many coatings comprising silver salts are transparent or translucent, and/or lack a colored appearance. Thus, when silver salt coatings are applied to transparent surfaces, the coated surfaces typically have little color and are highly transparent. While coatings comprising silver salts are often translucent, it is extremely difficult to solubilize silver salts and thus to directly deposit coatings comprising silver salts.

SUMMARY

The present disclosure is directed to methods for processing substrates having or carrying a coating comprising a metal. The methods include providing a substrate surface having a coating comprising a metal, and exposing the substrate surface to a mixture comprising an oxidizing agent and an anion.

The substrate surfaces can comprise plastic, glass, metal, ceramics, elastomers, or mixtures or laminates thereof. The substrate surfaces can comprise surfaces of medical devices or medical device components. Preferred examples of substrate surfaces include polycarbonate medical devices. The substrate surface also can comprise surfaces of medical fluid containers or medical fluid flow systems. Preferred examples of medical fluid flow systems include I.V. sets and components thereof, such as, for example, luer access devices.

The metallic coatings can comprise various metals or mixtures of metals. Preferred metals include silver, copper, gold, zinc, cerium, platinum, palladium, and tin. The coatings can comprise metallic nanoparticles.

Suitable oxidizing agents include various agents and mixtures of agents capable of oxidizing metals. Suitable oxidizing agents include, but are not limited to, metal ions and metal-containing compounds, halogens and halogen-containing compounds, and organic and inorganic compounds of oxygen.

Suitable anions include, but are not limited to, various organic and inorganic anions, and mixtures of anions. Suitable anions include halides, halogen-containing anionic compounds, nitrogen anions, and oxyanions, such as carboxylates and sulfates.

DETAILED DESCRIPTION

The present disclosure is directed to methods of processing substrates carrying coatings comprising a metal. The methods according to the invention involve providing a substrate surface carrying a coating comprising a metal and exposing the substrate surface to a mixture comprising an oxidizing agent and an anion. In one aspect, the metal can comprise metallic nanoparticles.

The substrate surfaces carrying coatings comprising a metal can be produced by a wide variety of known methods for coating surfaces with metals. Known techniques for producing such coatings include, for example, silver mirroring, chemical vapor deposition, physical vapor deposition (e.g., sputtering), e-beam deposition, electroplating, and solution coating. Suitable coating compositions for providing a substrate surface carrying a coating comprising a metal and methods for producing such coated substrates are disclosed, for example, in U.S. Pat. Nos. 6,126,931, 6,180,584, 6,264,936, 6,716,895, 7,179,849, 7,232,777, 7,288,264, and U.S. Patent Application Publication Nos. 2007/0003603, and 2007/0207335, the disclosures of which are hereby incorporated by reference in their entireties.

As previously discussed, many coatings comprising a metal are opaque, or exhibit a colored appearance. Thin film coatings comprising metallic silver, for example, can be brown in color, and thus substrates carrying such coatings can have a brown color and exhibit poor transparency. Exposing substrate surfaces carrying coatings comprising a metal to a mixture of an oxidizing agent and an anion according to the methods disclosed herein can advantageously increase the transparency of the coating comprising a metal, thereby providing, for example, an efficient method for obtaining medical devices comprising a more transparent antimicrobial coating. Accordingly, the disclosed methods advantageously increase the transparency of such coatings and hence the transparency of substrate surfaces carrying such coatings.

In contrast to coatings comprising metals, many coatings comprising metal salts and/or nanoparticles of metal salts are transparent or translucent, and/or lack a colored appearance. Thus, substrates carrying such coatings typically are clear or have a light color, and can be highly transparent. Exposing substrate surfaces carrying coatings comprising a metal to a mixture of an oxidizing agent and an anion according to the methods disclosed herein is envisioned to form metal salts and/or nanoparticles of metal salts comprising an oxidized form of the metal associated with the anion as a counterion. Accordingly, it is believed the disclosed methods can advantageously form metal salts and/or metal salt nanoparticles, thereby increasing the transparency of such coatings and hence the transparency of substrate surfaces carrying such coatings.

Furthermore, when the coatings initially comprise metallic nanoparticles, it is envisioned that the disclosed methods can increase the polydispersity of the nanoparticles (in the coatings) and thereby provide coatings capable of broader release profiles and thus of demonstrating sustained antimicrobial activity over time (at least relative to coatings which have not been treated in accordance with the inventive methods). By changing the polydispersity of the coatings initially comprising metallic nanoparticles, the disclosed methods are also believed to provide coatings capable of enhanced efficacy because such coatings include larger nanoparticles after exposure to a mixture of an oxidizing agent and an anion in accordance with the disclosure (at least relative to coatings which have not been treated in accordance with the inventive methods) and thus can demonstrate extended antimicrobial activity (at least relative to coatings which have not been treated in accordance with the inventive methods) because the larger particles are expected to dissolve more slowly relative to the smaller particles contained in the original coating.

The substrate surfaces of the present disclosure can comprise various materials including, for example, glasses, metals, plastics, ceramics, and elastomers, as well as mixtures and/or laminates thereof. Suitable examples of plastics include, but are not limited to, acrylonitrile butadiene styrenes, polyacrylonitriles, polyamides, polycarbonates, polyesters, polyetheretherketones, polyetherimides, polyethylenes such as high density polyethylenes and low density polyethylenes, polyethylene terephthalates, polylactic acids, polymethyl methyacrylates, polypropylenes, polystyrenes, polyurethanes, poly(vinyl chlorides), polyvinylidene chlorides, polyethers, polysulfones, silicones, and blends and copolymers thereof. Suitable elastomers include, but are not limited to, natural rubbers and synthetic rubbers, such as styrene butadiene rubbers, ethylene propylene diene monomer rubbers (EPDM), polychloroprene rubbers (CR), acrylonitrile butadiene rubbers (NBR), chlorosulfonated polyethylene rubbers (CSM), polyisoprene rubbers, isobutylene-isoprene copolymeric rubbers, chlorinated isobutylene-isoprene copolymeric rubbers, brominated isobutylene-isoprene copolymeric rubbers, and blends and copolymers thereof.

In one preferred embodiment of the present disclosure, the coating comprising a metal is present on (or carried by) a surface of a medical device or medical device component. Medical devices and medical device components which can benefit from the methods according to the disclosure, include, but are not limited to, instruments, apparatuses, implements, machines, contrivances, implants, and components and accessories thereof, intended for use in the diagnosis, cure, mitigation, treatment, or prevention of disease or other condition in humans or other animals, or intended to affect the structure or any function of the body of humans or other animals. Such medical devices are described, for example, in the official National Formulary, the United States Pharmacopoeia, and any supplements thereto. Representative medical devices include, but are not limited to: catheters, such as venous catheters, urinary catheters, Foley catheters, and pain management catheters; dialysis sets; dialysis connectors; stents; abdominal plugs; feeding tubes; indwelling devices; cotton gauzes; wound dressings; contact lenses; lens cases; bandages; sutures; hernia meshes; mesh-based wound coverings; surgical tools; medical monitoring equipment including, but not limited to the touch screen displays often used in conjunction with such equipment; medical pumps; pump housings; gaskets such as silicone O-rings; needles; syringes; surgical sutures; filtration devices; drug reconstitution devices; implants; metal screws; and metal plates. Additional exemplary medical devices include, but are not limited to, medical fluid containers, medical fluid flow systems, infusion pumps, and medical devices such as stethoscopes which regularly come into contact with a patient. One example of a medical fluid flow system is an intravenous fluid administration set, also known as an I.V. set, used for the intravenous administration of fluids to a patient. A typical I.V. set uses plastic tubing to connect a phlebotomized subject to one or more medical fluid sources, such as intravenous solutions or medicament containers. I.V. sets optionally include one or more access devices providing access to the fluid flow path to allow fluid to be added to or withdrawn from the IV tubing. Access devices advantageously eliminate the need to repeatedly phlebotomize the subject and allow for immediate administration of medication or other fluids to the subject, as is well known. Access devices can be designed for use with connecting apparatus employing standard luers, and such devices are commonly referred to as "luer access devices," "luer-activated devices," or "LADs." LADs can be modified with one or more features such as antiseptic indicating devices. Various LADs are illustrated in U.S. Pat. Nos. 5,242,432, 5,360,413, 5,730,418, 5,782,816, 6,039,302, 6,669,681, and 6,682,509, and U.S. Patent Application Publication Nos. 2003/0141477, 2003/0208165, 2008/0021381, and 2008/0021392, the disclosures of which are hereby incorporated by reference in their entireties.

I.V. sets can incorporate additional optional components including, for example, septa, stoppers, stopcocks, connectors, protective connector caps, connector closures, adaptors, clamps, extension sets, filters, and the like. Thus, additional suitable medical devices and medical device components which may be processed in accordance with the methods of the present disclosure include, but are not limited to: I.V. tubing, I.V. fluid bags, I.V. set access devices, septa, stopcocks, I.V. set connectors, I.V. set connector caps, I.V. set connector closures, I.V. set adaptors, clamps, I.V. filters, catheters, needles, stethoscopes, and cannulae. Representative access devices include, but are not limited to: luer access devices including, but not limited to, needleless luer access devices.

The surface of the medical device or medical device component can be fully or partially coated with the coating comprising a metal. The coating can be present on (or carried by) an exterior surface of the device (i.e., a surface which is intended to come into contact with a patient or healthcare provider), an interior surface of the device (i.e., a surface which is not intended to come into contact with a patient or healthcare provider, but which can come into contact with the patient's blood or other fluids), or both. Suitable medical devices and medical device components are illustrated in U.S. Pat. Nos. 4,412,834, 4,417,890, 4,440,207, 4,457,749, 4,485,064, 4,592,920, 4,603,152, 4,738,668, 5,630,804, 5,928,174, 5,948,385, 6,355,858, 6,592,814, 6,605,751, 6,780,332, 6,800,278, 6,849,214, 6,878,757, 6,897,349, 6,921,390, and 6,984,392, and U.S. Patent Application Publication No. 2007/0085036, the disclosures of which are hereby incorporated by reference in their entireties.

The coatings of the present disclosure can comprise metals having antimicrobial properties. Suitable metals for use in the coatings include, but are not limited to: silver, copper, gold, zinc, cerium, platinum, palladium, and tin. Coatings comprising a combination of two or more of the foregoing metals can also be used.

The antimicrobial activity of coatings comprising a metal can be affected by various physical properties of the coatings. When the original coating comprises metallic nanoparticles, the antimicrobial activity can be affected by physical properties such as the average size of the particles, the size distribution of the particles, the arrangement of the particles on the surface, and other factors. Exposing substrate surfaces carrying a coating comprising metallic nanoparticles to a mixture of an oxidizing agent and an anion according to the methods disclosed herein can alter the physical properties of the nanoparticles, for example, the particle sizes, thereby providing nanoparticle coatings having increased antimicrobial efficacy.

The antimicrobial activity of coatings comprising a metal can be affected by various chemical properties of the coatings, such as the incorporation of the anion in the coatings, the formation of metal salts comprising an oxidized form of the metal associated with the anion as a counterion, the composition of additional coating components, and other factors. Exposing substrate surfaces carrying a coating comprising a metal to a mixture of an oxidizing agent and an anion according to the methods disclosed herein can alter the chemical properties of the coatings, for example, by causing formation of salts, thereby coatings having increased antimicrobial efficacy.

When the original coating comprises metallic nanoparticles, the initial diameter of the metallic nanoparticles typically is from about 1 nm to about 1000 nanometers, from about 1 nm to about 100 nanometers, from about 10 nm to about 70 nanometers, and/or from about 30 nm to about 50 nanometers. In this regard, it has generally been found that existing metallic coatings (which have not been treated in accordance with the inventive methods) typically include nanoparticles which have a narrow size distribution (monodisperse), i.e., such coatings comprise nanoparticles of substantially the same diameter. For example, a substantial portion of the nanoparticles in a given coating which has not been treated in accordance with the inventive methods typically have a diameter within ±10 nm of each other, for example, at least 50%, at least 60%, at least 70%, or more of the nanoparticles have a diameter within ±10 nm of each other, for example, at least 50% of the nanoparticles have a diameter between about 30 nm and about 50 nm.

A broad size distribution of metallic nanoparticles often is desirable to modify the rate of release of metal ions from the substrate surface, thereby providing more uniform, sustained release of the metal ions from the coated substrate surface. The methods according to the disclosure typically produce coatings comprising nanoparticles between about 0.1 nm and about 500 nm, between about 1 nm and about 400 nm, between about 10 nm and about 300 nm, and/or between about 20 nm and about 200 nm, but of course the obtained size range largely depends upon the initial diameter of the metallic nanoparticles. It has generally been found that metallic coating compositions which have been treated in accordance with the inventive methods typically include nanoparticles of varying sizes (i.e., demonstrating polydispersity). For example, typically less than 50% the nanoparticles in a coating which has been treated in accordance with the inventive methods have a diameter within ±10 nm of each other, for example, less than 50%, less than 60%, less than 70%, or more of the nanoparticles have a diameter within ±10 nm of each other, for example, less than 50% of the nanoparticles have a diameter between about 30 nm and about 50 nm. Coatings comprising nanoparticles demonstrating relatively increased polydispersity are advantageous in that the aforementioned size distribution allows the coatings to advantageously demonstrate a broader release profile over an extended period of time.

Processing Methods

The oxidizing agents of the present disclosure include a wide variety of known agents for oxidizing metals. Suitable oxidizing agents include metal ions and metal-containing compounds, such as $Fe^{3+}$, $Fe^{2+}$, $Cu^{2+}$, $Cu^+$, $MnO_4^-$, and $Ce^{4+}$; halogens and halogen-containing compounds, such as $IO_3^-$, $I_3^-$, $I_2$, $BrO_3^-$, $Br_2$, $Br_3^-$, $ClO_3^-$ and $Cl_2$; inorganic and organic compounds of oxygen, such as $NO_3^-$, $O_2$, $S_2O_8^{2-}$, $H_2O_2$, quinones, and fumarate; and methylene blue. Mixtures of oxidizing agents also are included. It should be understood that any known oxidizing agent could be used provided it has a sufficient oxidation potential to at least partially oxidize the metal included in the coating. Various concentrations of the oxidizing agent can be used, and these oxidizing agent concentrations can be readily determined by one of ordinary skill. Typical amounts of oxidizing agent can range from about 0.0001 M to about 5 M, for example, about 0.001 M to about 5 M, about 0.01 M to about 2.5 M, about 0.05 M to about 1 M, and/or about 0.1 M to about 0.5 M, but higher and lower concentrations of oxidizing agents also can be used.

The anions of the present disclosure include a wide variety of known anions, including organic and inorganic anions. Suitable anions include carboxylates, such as acetate, citrate, deoxycholate, fatty acid anions (e.g., decanoate, laurate, myristate, palmitate, stearate, eicosanoate, docsanoate, tetracosanoate, α-linolenate, stearidonate, eicosapentaenoate, docosahexaenoate, linoleate, γ-linolenate, dihomo-γ-linolenate, arachidonate, oleate, erucate, and nervonate), succinate, anionic carboxymethylcellulose, and alginate; halides, such as, fluoride, chloride, bromide, and iodide; halogen-containing anionic compounds, such as chlorate, bromate, and iodate; organic and inorganic oxyanions such as hydroxide, carbonate, oxalate, phosphates, pyrophosphates, phosphonates, phospholipids, sulfates, sulfonates, and cyanate; and nitrogen anions such as amide anions, sulfadiazine anions, cyanates, and cyanides. Mixtures of anions may also be used. Various concentrations of the anion can be used, and these anion concentration can be readily determined by one of ordinary skill. Typical amounts of anion can range from about 0.0001 M to about 10 M, for example, about 0.001 M to about 7 M, about 0.01 M to about 5 M, about 0.05 M to about 2.5 M, and/or about 0.1 M to about 1 M, but higher and lower concentrations of anions also can be used.

In one embodiment, the oxidizing agent and the anion of the present disclosure can be the same. Examples of such "dual oxidizing agents/anions" include chlorate ($ClO_3^-$), bromate ($BrO_3^-$), and iodate ($IO_3^-$). The oxidizing agent and/or the anion also can be generated in situ, for example, by dissolution of a salt in a solution, by protonation or deprotonation, or by a reaction that produces the oxidizing agent and/or anion. For example, $FeCl_3$ can dissolve in aqueous solution to form $Fe^{3+}$ as an oxidizing agent and $Cl^-$ as an anion, or $I_2$ can react in aqueous solution to form $H_2OI^+$ and iodide (I⁻) as an anion. An equilibrium reaction also can generate the oxidizing agent and/or the anion.

In another embodiment, the mixture of the present disclosure further comprises a polymeric additive. One example of a suitable polymeric additive is polyvinyl pyrrolidone.

In one embodiment of the present disclosure, the substrate surface can be exposed to povidone iodine. Povidone iodine comprises a complex of molecular iodine ($I_2$) with polyvinyl pyrrolidone (PVP). Molecular iodine is a known oxidizing agent, and as discussed above, iodide anion can be obtained in aqueous solution, for example, from reaction of $I_2$ and water so as to generate the requisite anion in situ. In another embodiment, the substrate surface can be exposed to povidone iodine by itself.

The substrate surfaces of the present disclosure can be exposed to the mixture comprising the oxidizing agent and anion by various known methods. Typical methods for exposing the substrate surface to the mixture comprising the oxidizing agent and anion include dipping, immersing, soaking, submerging, swabbing, spraying, washing, or otherwise contacting the substrate surface with the mixture comprising the oxidizing agent and the anion. The substrate surfaces can be exposed to the mixture comprising the oxidizing agent and the anion for various periods of time. The length of desired exposure can be readily determined by one of ordinary skill, and can vary depending on the reactivity of the mixture comprising the oxidizing agent and the anion and/or the desired properties of the final coating composition. Typically, the substrate surface is exposed for about 0.1 seconds to about 24 hours, but shorter and longer exposure periods can be used. Generally, the substrate surface is exposed to the mixture of the oxidizing agent and anion for about 0.1 seconds to about 2 hours, about 0.5 seconds to about 1 hour, about 1 second to about 30 minutes, and/or about 1 minute to about 10 minutes. The substrate surfaces also can be sequentially exposed to more than one mixture comprising an oxidizing agent and an anion, the second mixture of which may be the same as or different from the first mixture. When the second mixture is different from the first mixture, multicomponent coatings comprising more than one metal salt can be obtained. Such multicomponent coatings can demonstrate improved antimicrobial efficacy, improved antimicrobial specificity, and/or improved elution profiles. Short exposure times, for example, less than about 5 seconds, can be advantageous in producing one or more of the coatings of a multicomponent coating. Short exposure times can result in incomplete conversion of the metal to metal salts, allowing the remaining unreacted metal to be converted to a metal salt in a subsequent coating step.

After processing a substrate surface having a coating comprising a metal in accordance with the present methods, the metal content (including metal and metal ions) of the processed coating is typically at least 5% of the metal content of the original coating (prior to processing the substrate surface in accordance with the present methods). Generally, the metal content after processing by exposure to the mixture of the oxidizing agent and the anion is more than 5% of the metal content prior to exposure. For example, the metal content after exposure can be at least 10%, at least 20%, or at least 40% of the metal content prior to processing. After processing a substrate surface having a coating comprising a metal in accordance with the present methods, the coating also can have an increased amount of the anion, compared to the amount of anion in the coating prior to processing by exposure to the mixture of the oxidizing agent and the anion.

The disclosure may be better understood by reference to the following examples which are not intended to be limiting, but rather only set forth exemplary embodiments in accordance with the disclosure.

EXAMPLES

Example 1

Processing Silver Nanoparticle-Coated Polycarbonate Surfaces with Chloride Anions Polycarbonate surfaces having coatings comprising metallic silver nanoparticles were analyzed by transmission electron microscopy (TEM) to determine the initial size range of the silver nanoparticles. First, the silver coating was removed from the polycarbonate surface by rinsing the surface with dichloromethane. The rinse suspension was then centrifuged to separate the silver nanoparticles from the soluble organic components. The supernate was discarded, and the pellet of particles was resuspended in dichloromethane. The suspension was then applied to a carbon film supported on a TEM grid, and the initial size range of the silver nanoparticles was determined by TEM to be about 25 nm to about 50 nm in diameter These polycarbonate surfaces having coatings comprising metallic silver nanoparticles of 25 nm to 50 nm in diameter were exposed to a solution including an oxidizing agent and a chloride ion source. The oxidizing agent was varied as described herein. As a control, one silver-coated polycarbonate sample (1A) was not exposed to a solution containing an oxidizing agent and a chloride ion source. For the remaining samples (1B-1F), five aqueous 10 mL solutions were prepared having the final compositions shown in Table 1. The pH of the solutions was measured (see Table 1), and the solutions were added to glass vials with a screw cap. A silver-coated polycarbonate sample was added to the vials and incubated at room temperature in the solution for 15 to 70 minutes, as indicated in Table 1. After exposure to the solution containing an oxidizing agent and a chloride ion source, the polycarbonate sample was removed from the vial, rinsed with distilled water, and dried with pressurized air.

After exposure to the oxidizing agent and chloride ion source, the initially brown polycarbonate surfaces (Sample 1A) were rendered light yellow or colorless (Samples 1B-1F), as assessed by visual inspection.

The transparency of Samples 1A-1F was assessed by transmitted light photography. Transmitted light photographs of the samples were converted to digital grayscale images for analysis. To determine and the intensity of light ($I_0$) in the absence of the sample, a rectangular area of the image near the sample and representative of the background was selected. Typically, the rectangular area contained approximately 1000 pixels. A histogram displaying a graph of pixel intensity for the selected area was examined, and the mean pixel area was recorded as $I_0$. To determine and the intensity of light (I) that passed through the sample, a rectangular area of the same size and representative of the sample was selected. A histogram displaying a graph of pixel intensity for the selected area was examined, and the mean pixel area was recorded as I. The relative grayscale value of the sample was defined as: $-\log(I/I_0)$. Lower relative grayscale values, therefore, demonstrate that a higher fraction of light is transmitted through the substance.

Relative grayscale values for Samples 1A to 1F are provided in Table 1. The use of iodate (Sample 1C), hydrogen peroxide (Sample 1D), or persulfate at low pH (Sample 1F) as the oxidizing agent produced highly transparent polycarbonate surfaces (relative grayscale value <0.2) after processing in accordance with the disclosed methods, as compared to the transparency of an untreated coated control (Sample 1A, relative grayscale value=0.67).

TABLE 1

| Sample | Composition | pH | Exposure time (minutes) | Relative Grayscale Value |
|---|---|---|---|---|
| 1A | Untreated coated control | — | — | 0.67 |
| 1B | 0.5 M $FeCl_3$ | <1 | 15 | 0.25 |
| 1C | 0.3 M $KIO_3$; 0.6 N HCl | <1 | 25 | 0.15 |
| 1D | 1.5 M $H_2O_2$; 4.5 M NaCl | 4.8 | 50 | 0.17 |
| 1E | 0.26 M $Na_2S_2O_8$; 2.5 M NaCl | 8.1 | 70 | 0.21 |
| 1F | 0.52 M $Na_2S_2O_8$; 2.5 M NaCl; 0.1 N HCl | 1 | 50 | 0.19 |

Energy dispersive x-ray (EDX) spectroscopy was performed to determine the composition of the coatings after exposure to the oxidizing agent and chloride ion. As shown by the normalized peak areas in Table 2, silver remained on the surfaces for all oxidizing conditions tested. More specifically, the silver content of the surfaces exposed to oxidizing agent solutions was about 50% of the original silver content for the unexposed control sample. In addition, the EDX spectra showed an increase of chloride ion on the surfaces exposed to the oxidizing agent solutions compared to the unexposed control silver-coated surface (see Table 2). These data are consistent with a mixture of metallic silver and crystalline silver chloride.

TABLE 2

| Sample | Composition | Normalized Ag | Cl/Ag ratio |
|---|---|---|---|
| 1A | Untreated coated control | 1.00 | 0.00 |
| 1B | 0.5 M $FeCl_3$ | 0.57 | 0.12 |
| 1C | 0.3 M $KIO_3$; 0.6 N HCl | 0.48 | 0.33 |
| 1D | 1.5 M $H_2O_2$; 4.5 M NaCl | 0.52 | 0.20 |
| 1E | 0.26 M $Na_2S_2O_8$; 2.5 M NaCl | 0.52 | 0.00 |
| 1F | 0.52 M $Na_2S_2O_8$; 2.5 M NaCl; 0.1 N HCl | 0.63 | 0.38 |

Transmission electron microscopy (TEM) was used to determine the size of the silver nanoparticles after exposure to $FeCl_3$ according to the methods described above. The particles after exposure were found to be larger in size and more polydisperse than before exposure to the oxidizing agent and chloride ion, typically ranging in size from about 25 nm to about 200 nm.

Example 2

Processing Silver Nanoparticle-Coated Polycarbonate Surfaces with Halides to Prepare Multicomponent Coatings Polycarbonate surfaces coated with metallic silver nanoparticles of about 25 nm to about 50 nm in diameter were sequentially exposed to a series of oxidizing agent solutions having different anion sources according to the following general procedure. Aqueous 10 mL solutions were prepared containing an oxidizing agent and an anion source, both of which were varied in the different solutions. The pH of the solutions was measured, and the solutions were added to glass vials with a screw cap. A silver-coated polycarbonate sample was added to the first vial and incubated at room temperature in the solution for 35 minutes. After exposure to the first solution, the polycarbonate sample was removed from the vial, rinsed with distilled water, and briefly exposed (<1 second-2 seconds) to the second solution. The polycarbonate sample was then rinsed with distilled water, and exposed to the third solution for 20-30 seconds. The sample was rinsed with distilled water, and dried with pressurized air.

In one set of conditions (Sample 2A), the silver nanoparticle-coated surface was exposed to a first solution (pH<1) containing 0.54 M $Na_2S_2O_8$ and 2.5 M NaCl for 35 minutes. The surface was next exposed to a second solution (pH=3.1) containing 0.38 M $Na_2S_2O_8$ and 0.5 M KBr for 2 seconds. Lastly, the surface was exposed to a third solution (pH=4.1) containing 0.075 M $Na_2S_2O_8$ and 0.012 M KI for 20 seconds.

In another set of conditions (Sample 2B), the silver nanoparticle-coated surface was exposed to a first solution (pH<1) containing 0.54 M $Na_2S_2O_8$ and 2.5 M NaCl for 35 minutes. The surface was next exposed to a second solution (pH=3.1) containing 0.38 M $Na_2S_2O_8$ and 0.5 M KBr for less than 1 second. Lastly, the surface was exposed to a third solution (pH=4.1) containing 0.075 M $Na_2S_2O_8$ and 0.012 M KI for 30 seconds.

As a control, one silver-coated polycarbonate sample (Sample 2C) was not exposed to solutions containing oxidizing agents and anions. An additional control (Sample 2D) was not coated with silver, nor exposed to solutions containing oxidizing agents and anions.

After exposure to the solutions, the initially brown silver-coated polycarbonate surfaces (Sample 2C) were rendered pale yellow or colorless (Samples 2A and 2B), as assessed by visual inspection. The transparency of Samples 2A-2D was assessed as described for Example 1 (see Table 3). After exposure to either set of conditions described above, Samples 2A and 2B were highly transparent (relative grayscale value<0.15), as compared to the transparency of an untreated coated control (Sample 2C, relative grayscale value=0.46), and appeared substantially similar in transparency to Sample 2D (relative grayscale value=0.04), a surface lacking any silver nanoparticle coating.

TABLE 3

| Sample | Conditions | Relative Grayscale Value |
|---|---|---|
| 2A | $Na_2S_2O_8$ and NaCl solution for 35 minutes<br>$Na_2S_2O_8$ and KBr solution for 2 seconds<br>$Na_2S_2O_8$ and KI solution for 20 seconds | 0.11 |
| 2B | $Na_2S_2O_8$ and NaCl solution for 35 minutes<br>$Na_2S_2O_8$ and KBr solution for <1 second<br>$Na_2S_2O_8$ and 0.012 solution for 30 seconds | 0.07 |
| 2C | Untreated coated control | 0.46 |
| 2D | Untreated uncoated control | 0.04 |

Energy dispersive x-ray (EDX) spectroscopy was performed to determine the composition of the coatings after exposure to the oxidizing agent solutions. As shown in Table 4, silver remained on the surfaces for both sets of conditions described above. In addition, the EDX spectra showed the presence of chloride, bromide, and iodide on the surfaces exposed to the oxidizing agent solutions (Samples 2A and 2B), but not on the unexposed control silver-coated surface (Sample 2C).

TABLE 4

| Sample | Normalized Ag | Br/Ag ratio | Cl/Ag ratio | I/Ag ratio |
|---|---|---|---|---|
| 2C | 1 | 0.0 | 0.0 | 0.0 |
| 2A | 0.73 | 0.87 | 0.16 | 0.085 |
| 2B | 0.70 | 0.86 | 0.24 | 0.091 |

Example 3

Antimicrobial Properties of Processed Silver Coatings

Polycarbonate surfaces having coatings comprising metallic silver nanoparticles of 25 nm to 50 nm in diameter were exposed to various conditions in accordance with the methods of the present disclosure. As a control, one silver-coated polycarbonate sample (3A) was not processed according to the methods disclosed herein. An additional control (Sample 3F) was not coated with silver, nor exposed to solutions containing oxidizing agents and anions. For samples 3B-3D, three aqueous 15 mL solutions were prepared having the final compositions shown in Table 5. The pH of the solutions was measured (see Table 5), and the solutions were added to glass vials with a screw cap. A silver-coated polycarbonate sample was added to the vials and incubated at room temperature in the solution for 5 to 60 minutes, as indicated in Table 5. After exposure to the solution containing an oxidizing agent and a chloride ion source, the polycarbonate sample was removed from the vial, rinsed with distilled water, and dried with pressurized air.

TABLE 5

| Sample | Composition | pH | Exposure time (minutes) |
|---|---|---|---|
| 3A | Untreated coated control | — | — |
| 3B | 0.54 M $Na_2S_2O_8$; 2.5 M NaCl | 4 | 60 |
| 3C | 0.38 M $Na_2S_2O_8$; 0.5 M KBr | 3.1 | 15 |
| 3D | 0.075 M $Na_2S_2O_8$; 0.012 M KI | 4 | 5 |
| 3E | 0.38 M $Na_2S_2O_8$; 2.5 M NaCl | 4 | 30 |
|  | 0.38 M $Na_2S_2O_8$; 0.5 M KBr | 3.1 | 0.016 |
|  | 0.051 M $Na_2S_2O_8$; 0.08 M KI | 4 | 0.25 |
| 3F | Untreated uncoated control | — | — |

Sample 3E, a multicomponent coating, was prepared according to the general procedure of Example 2, with the following exceptions: the aqueous solutions were 15 mL, and the exposure times differed. Specifically, as indicated in Table 5, the silver nanoparticle-coated surface was exposed to a first solution (pH=4) containing 0.38 M $Na_2S_2O_8$ and 2.5 M NaCl for 30 minutes. The surface was next exposed to a second solution (pH=3.1) containing 0.38 M $Na_2S_2O_8$ and 0.5 M KBr for 1 second. Lastly, the surface was exposed to a third solution (pH=4) containing 0.051 M $Na_2S_2O_8$ and 0.08 M KI for 15 seconds.

The antimicrobial activity of Samples 3A-3E against *Staphylococcus aureus* (*S. aureus*) was tested. A suspension of *S. aureus* was grown in tryptic soy broth for 18-24 hours. The suspension was then diluted in saline to $6.4 \times 10^5$ colony-forming units per mL (cfu/mL). Tubes containing 5 mL saline were inoculated with 0.1 mL ($6.4 \times 10^4$ cfu) of the suspension. Samples 3A-3F were aseptically added to the tubes, which were incubated at 20-25° C. for 48 hours. The samples then were plated in tryptic soy agar in triplicate and incubated at 30-35° C. for 48 hours. After this time, growth of *S. aureus* was measured, as shown in Table 6.

TABLE 6

| Sample | Sample 1 Recovery (cfu) | Sample 2 Recovery (cfu) | Sample 3 Recovery (cfu) | Average (cfu) | log (Average) |
|---|---|---|---|---|---|
| 3A | $1.36 \times 10^3$ | $1.24 \times 10^3$ | $2.5 \times 10^3$ | $1.7 \times 10^3$ | 3.23 |
| 3B | $1.1 \times 10^1$ | $1.1 \times 10^2$ | $5.2 \times 10^3$ | $1.8 \times 10^3$ | 3.26 |
| 3C | $1.8 \times 10^1$ | $1.02 \times 10^3$ | $6.3 \times 10^2$ | $5.6 \times 10^2$ | 2.75 |
| 3D | $4.7 \times 10^1$ | $3.3 \times 10^2$ | $3.4 \times 10^2$ | $2.4 \times 10^2$ | 2.38 |
| 3E | $8.2 \times 10^1$ | $8.4 \times 10^2$ | $2.9 \times 10^2$ | $4.0 \times 10^2$ | 2.60 |
| 3F | $4.3 \times 10^4$ | $4.0 \times 10^4$ | $3.3 \times 10^4$ | $3.9 \times 10^4$ | 4.59 |

The silver-coated Samples 3A-3E demonstrated antimicrobial activity against *S. aureus*, as determined by a comparison of *S. aureus* recovery from samples 3A-3E to *S. aureus* recovery from a substrate lacking a silver coating (Sample 3F). The silver coatings processed accorded to the disclosed methods (Samples 3B-3E) showed antimicrobial activity equal to or greater than an unprocessed silver-coated surface (Sample 3A). In particular, the surface carrying a coating comprising bromide (Sample 3C), the surface carrying a coating comprising iodide (Sample 3D), and the surface carrying a multicomponent coating (Sample 3E) all demonstrated improved (3- to 7-fold) antimicrobial activity compared to Sample 3A.

Example 4

Processing of Silver Nanoparticle-Coated Polycarbonate Surfaces with Povidone Iodine Polycarbonate surfaces having an antimicrobial coating comprising silver metallic nanoparticles were exposed to povidone iodine (PVP-iodine) ointment (10.5 wt. % povidone iodine, 80% v/v glycerin). As a control, one silver-coated polycarbonate surface (Sample 4A) was not processed according to the methods disclosed herein. As a second control, a silver-coated polycarbonate surface was soaked in normal saline for 24 hours (Sample 4B). Both samples (4A and 4B) were brown in color. A silver-coated polycarbonate surface that was swabbed with PVP-iodine ointment and then soaked in normal saline for 24 hours (Sample 4C) also was brown in color. Sample 4D was soaked in PVP-iodine ointment for 10 minutes, and was then soaked in normal saline for 24 hours. Sample 4E was soaked in PVP-iodine ointment for 24 hours. After the 24 hour soaking period, both Samples 4D and 4E were rinsed with deionized water. Soaking of Samples 4D and 4E in PVP-iodine ointment according to the procedure above resulted in nearly complete loss of color from the silver-coated surfaces, as assessed by visual inspection.

The transparency of Samples 4A-4E was assessed as described for Example 1 (see Table 7). Exposure of the samples to PVP-iodine ointment for 10 minutes (4D) or 24 hours (4E) produced highly transparent polycarbonate surfaces, as shown in Table 7.

TABLE 7

| Sample | Conditions | Relative Grayscale Value |
|---|---|---|
| 4A | Untreated coated control | 0.6 |
| 4B | Coated control, soaked in saline 24 hrs | 0.6 |
| 4C | Swabbed with povidone iodine ointment, then soaked in saline 24 hrs | 0.4 |
| 4D | Soaked in povidone iodine ointment 10 minutes, then soaked in saline 24 hrs | 0.1 |
| 4E | Soaked in povidone iodine ointment 24 hrs | 0.1 |

Elemental analysis of Samples 4D and 4E by energy dispersive x-ray spectrometry (EDX) showed that silver remained on the sample surfaces after soaking in PVP-iodine ointment (see Table 8). As provided in Table 8, the analysis further showed the gain of iodine on the PVP-iodine ointment-soaked surfaces (Samples 4D and 4E), but not on the surface swabbed with PVP-iodine ointment (Sample 4C).

TABLE 8

| Sample | Conditions | Normalized Ag | I/Ag ratio |
|---|---|---|---|
| 4B | Coated control, soaked in saline 24 hrs | 1.00 | 0.0 |
| 4C | Swabbed with PVP-iodine ointment, then soaked in saline 24 hrs | 0.47 | 0.0 |
| 4D | Soaked in PVP-iodine ointment 10 minutes, then soaked in saline 24 hrs | 0.93 | 0.82 |
| 4E | Soaked in p PVP-iodine ointment 24 hrs | 0.74 | 0.73 |

Example 5

Processing of Silver Nanoparticle-Coated Polycarbonate Surfaces with Dilute Povidone Iodine Ointment Polycarbonate surfaces having an antimicrobial coating comprising silver metallic nanoparticles were exposed to a diluted disinfectant solution of povidone iodine (PVP-iodine) ointment. The PVP-iodine ointment (10.5 wt. % povidone iodine, 80% v/v glycerin) was diluted 1:10 in water, and Samples 5B-5F were incubated in the diluted PVP-iodine solution for the following periods of time: 30 minutes (Sample 5B), 1 hour (Sample 5C), 2 hours (Sample 5D), 4 hours (Sample 5E), and 24 hours (Sample 5F). As a control, one silver-coated polycarbonate sample (5A) was not exposed to PVP-iodine. After exposure to solutions containing PVP-iodine, the surfaces were nearly colorless and substantially similar in color to a surface lacking any silver nanoparticle coating, as assessed by visual inspection.

The transparency of Samples 5A-5F was assessed as described for Example 1 (see Table 9). Exposure of the samples to povidone iodine for various periods of time ranging from 30 minutes to 24 hours (Samples 5B-5F) produced highly transparent polycarbonate surfaces compared to a silver-coated surface not exposed to povidone iodine (Sample 5A), as shown in Table 9.

TABLE 9

| Sample | Length of Exposure to Diluted PVP-iodine (hrs) | Relative Grayscale Value |
|---|---|---|
| 5A | Untreated coated control | 0.6 |
| 5B | 0.5 | 0.1 |
| 5C | 1 | 0.1 |
| 5D | 2 | 0.1 |
| 5E | 4 | 0.1 |
| 5F | 24 | 0.1 |

Example 6

Processing of Silver Nanoparticle-Coated Polycarbonate Surfaces with Varying Amounts of Povidone Iodine Polycarbonate surfaces having an antimicrobial coating comprising silver metallic nanoparticles were exposed to disinfectant solutions containing varying amounts of povidone iodine (PVP-iodine) ointment (10.5 wt. % povidone iodine, 80% v/v glycerin). The povidone iodine ointment was diluted in 10 mL of water according to the amounts provided in Table 10, and Samples 6A-6D were incubated in the povidone iodine solutions for 10 minutes. After exposure to the solutions, the surfaces were less colored or nearly colorless, as assessed by visual inspection.

TABLE 10

| Sample | 10.5% Povidone Iodine Ointment (g) | Relative Grayscale Value |
|---|---|---|
| 6A | 0.073 | 0.2 |
| 6B | 0.617 | 0.1 |
| 6C | 1.256 | 0.1 |
| 6D | 2.489 | 0.1 |

The transparency of Samples 6A-6D was assessed as described for Example 1 (see Table 10). Exposure of the samples to varying amounts povidone iodine for 10 minutes produced highly transparent polycarbonate surfaces (relative grayscale value<0.15), as compared to a silver-coated surface not exposed to povidone iodine (see Example 5 Sample 5A, having relative grayscale value=0.6), as shown in Table 10.

Example 7

Processing of Silver Nanoparticle-Coated Polycarbonate Surfaces with BETADINE®

Polycarbonate surfaces having an antimicrobial coating comprising silver metallic nanoparticles were exposed to a disinfectant solution containing 5% by weight of BETADINE® solution (10% povidone iodine). Samples were incubated in the BETADINE® solution for 15 minutes, and transparency was assessed as described for Example 1. After exposure to the BETADINE® solution, the relative grayscale value decreased from 0.8 to 0.2.

Example 8

Processing of Silver Nanoparticle-Coated Polycarbonate Surfaces with Povidone Iodine Polycarbonate surfaces having an antimicrobial coating comprising silver metallic nanoparticles were exposed to various povidone iodine (PVP-iodine) ointment-containing solutions for 3-24 hours according to the conditions provided in Table 11. As a control, one silver-coated polycarbonate surface (Sample 8A) was not exposed to an PVP iodine-containing solution. Elemental analysis of Samples 8A-8E by energy dispersive x-ray spectrometry (EDX) was used to monitor silver and iodine content.

TABLE 11

| Sample | Composition | Exposure Time (hrs) | Normalized Ag | I/Ag ratio |
|---|---|---|---|---|
| 8A | Untreated coated control | — | 1.00 | 0.00 |
| 8B | PVP-iodine ointment | 24 | 0.78 | 0.84 |
| 8C | PVP-iodine ointment | 3 | 0.80 | 0.73 |
| 8D | 10% v/v PVP-iodine ointment in water | 24 | 0.82 | 0.87 |
| 8E | 10% v/v PVP-iodine ointment in water | 3 | 0.65 | 0.81 |

After exposure to PVP-iodine ointment for 3 or 24 hours (Sample 8B or 8C), both silver and iodide were found to be present on the surface. Exposure of the samples to 10% PVP-iodine ointment for 3 or 24 hours (Sample 8D or 8E) also produced surfaces containing both silver and iodide.

Example 9

Processing of Silver-Coated Polycarbonate Surfaces with BETADINE®

A polycarbonate surface was sputtered with silver for 120 seconds to obtain a semi-transparent silver coating (Sample 9A). The substrate was cut into two pieces and each piece was exposed to a disinfectant solution of 5% by weight BETADINE® solution (10% povidone iodine) in water for 60 and 120 seconds (Samples 9B and 9C, respectively). The resulting change in relative grayscale value was from 0.2 to 0.1 (Sample 9B) and to 0.0 (Sample 9C). Energy dispersive x-ray (EDX) spectroscopy was performed before and after exposure to the disinfectant solution, and confirmed that a coating containing a halide was produced (see Table 12).

TABLE 12

| Sample | Conditions | Relative Grayscale Value | Normalized Ag | I/Ag ratio |
|---|---|---|---|---|
| 9A | Untreated coated control | 0.2 | 1.00 | 0.00 |
| 9B | 5% BETADINE ®, 60 sec | 0.1 | 0.76 | 0.48 |
| 9C | 5% BETADINE ®, 120 sec | 0.0 | 0.75 | 0.67 |

As shown in Table 12, substrate surfaces carrying a coating comprising metallic silver were found to retain silver and gain iodide when processed according to the methods disclosed herein.

What is claimed is:

1. A method for processing a substrate having a coating comprising a metal comprising: providing a substrate surface having a coating comprising a metal in a non-oxidized form, and exposing the substrate surface to a mixture comprising an oxidizing agent and an anion, wherein the anion is a halide, and the substrate surface comprises a surface of a medical device or medical device component.

2. The method of claim 1, wherein the substrate surface comprises at least one plastic, glass, metal, ceramic, elastomer, or mixtures or laminates thereof.

3. The method of claim 1, wherein the substrate surface comprises a plastic or elastomer selected from the group consisting of: acrylonitrile butadiene styrenes, polyacrylonitriles, polyamides, polycarbonates, polyesters, polyetheretherketones, polyetherimides, polyethylenes, polyethylene terephthalates, polylactic acids, polymethyl methyacrylates, polypropylenes, polystyrenes, polyurethanes, poly(vinyl chlorides), polyvinylidene chlorides, polyethers, polysulfones, silicones, natural rubbers, synthetic rubbers, styrene butadiene rubbers, ethylene propylene diene monomer rubbers, polychloroprene rubbers, acrylonitrile butadiene rubbers, chlorosuphonated polyethylene rubbers, polyisoprene rubbers, isobutylene-isoprene copolymeric rubbers, chlorinated isobutylene-isoprene copolymeric rubbers, brominated isobutylene-isoprene copolymeric rubbers, and blends and copolymers thereof.

4. The method of claim 1, wherein the substrate surface comprises a surface of a medical fluid container or medical fluid flow system.

5. The method of claim 1, wherein the substrate surface comprises a surface of an I.V. set.

6. The method of claim 1, wherein the substrate surface comprises a surface of a medical device or medical device component selected from the group consisting of: I.V. tubing, I.V. fluid bags, access devices for I.V. sets, septa, stopcocks, I.V. set connectors, I.V. set adaptors, clamps, I.V. filters, catheters, needles, and cannulae.

7. The method of claim 1, wherein the substrate surface comprises a surface of a luer access device or a needleless luer access device.

8. The method of claim 1, wherein the substrate surface comprises an antimicrobial metal coating.

9. The method of claim 1, wherein the metal comprises silver, copper, gold, zinc, cerium, platinum, palladium, tin, or mixtures thereof.

10. The method of claim 1, wherein the metal comprises silver.

11. The method of claim 1, wherein the metal comprises metallic nanoparticles.

12. The method of claim 11, wherein the metallic nanoparticles have an initial diameter of about 1 nm to about 1000 nanometers.

13. The method of claim 1, wherein the exposing occurs for about 0.1 seconds to about 24 hours.

14. The method of claim 1, wherein the exposing occurs for about 0.1 seconds to about 2 hours.

15. The method of claim 1, wherein the oxidizing agent is selected from the group consisting of: metal ions, metal compounds, halogens, halogen-containing compounds, organic compounds of oxygen, inorganic compounds of oxygen, and mixtures thereof.

16. The method of claim 1, wherein the oxidizing agent is selected from the group consisting of: $Fe^{3+}$, $Fe^{2+}$, $Cu^{2+}$, $Cu^+$, $MnO_4^-$, $Ce^{4+}$, $IO_3^-$, $I_3^-$, $I_2$, $BrO_3^-$, $Br_2$, $Br_3^-$, $ClO_3^-$, $Cl_2$, $NO_3^-$, $O_2$, $S_2O_8^{2-}$, $H_2O_2$, quinones, fumarate, methylene blue, and mixtures thereof.

17. The method of claim 1, wherein the anion is selected from the group consisting of: fluoride, chloride, bromide, iodide, and mixtures thereof.

18. The method of claim 1, wherein the oxidizing agent and the anion are the same.

19. The method of claim 1, wherein the exposing comprises exposing the substrate surface to povidone iodine.

20. The method of claim 1, wherein the exposing comprises exposing the substrate surface to more than one mixture comprising an oxidizing agent and an anion.

21. The method of claim 1, wherein the coating prior to said exposing has a first metal content, the coating after said exposing has a second metal content, and the second metal content is at least 5% of the first metal content.

22. The method of claim 1, wherein the coating prior to said exposing has a first metal content, the coating after said exposing has a second metal content, and the second metal content is at least 10% of the first metal content.

23. The method of claim 1, wherein the coating prior to said exposing has a first metal content, the coating after said exposing has a second metal content, and the second metal content is at least 20% of the first metal content.

24. The method of claim 1, wherein the coating prior to said exposing has a first metal content, the coating after said exposing has a second metal content, and the second metal content is at least 40% of the first metal content.

25. The method of claim 1, wherein the coating prior to said exposing has a first anion content, the coating after said exposing has a second anion content, and the second anion content is increased compared to the first anion content.

26. The method of claim 1, wherein the mixture further comprises a polymeric additive.

27. The method of claim 26, wherein the polymeric additive comprises polyvinyl pyrrolidone.

* * * * *